US010786387B2

(12) United States Patent
Mooney

(10) Patent No.: US 10,786,387 B2
(45) Date of Patent: Sep. 29, 2020

(54) DISPOSABLE URINATION DEVICE FOR WOMEN

(71) Applicant: James John Mooney, Pittsburgh, PA (US)

(72) Inventor: James John Mooney, Pittsburgh, PA (US)

(73) Assignee: James Mooney, LLC, Pittsburgh, PA (US)

(*) Notice: Subject to any disclaimer, the term of this patent is extended or adjusted under 35 U.S.C. 154(b) by 0 days.

(21) Appl. No.: 16/039,868

(22) Filed: Jul. 19, 2018

(65) Prior Publication Data
US 2019/0046349 A1 Feb. 14, 2019

Related U.S. Application Data

(60) Provisional application No. 62/545,116, filed on Aug. 14, 2017.

(51) Int. Cl.
A61F 5/455 (2006.01)
A61F 5/44 (2006.01)

(52) U.S. Cl.
CPC .......... A61F 5/4556 (2013.01); A61F 5/4404 (2013.01); A61F 5/4553 (2013.01); A61F 2005/4402 (2013.01)

(58) Field of Classification Search
CPC .... A61F 5/4556; A61F 5/4404; A61F 5/4553; A61F 5/455; A61F 2005/4402; A61G 9/006; A47K 11/12; A61B 10/007
See application file for complete search history.

(56) References Cited

U.S. PATENT DOCUMENTS

| | | | |
|---|---|---|---|
| 940,756 A * | 11/1909 | Van Vechten | A61F 5/4556 4/144.4 |
| 4,023,216 A * | 5/1977 | Li | A61F 5/4556 4/144.3 |
| 4,108,222 A * | 8/1978 | Kaufman | B67C 11/02 141/337 |
| 4,528,703 A | 7/1985 | Kraus | |
| 4,626,249 A | 12/1986 | Hamey | |
| 4,751,751 A | 6/1988 | Reno | |
| 4,937,889 A | 7/1990 | Strickland | |
| 5,330,453 A * | 7/1994 | Cornellier | A61F 5/4556 222/527 |
| 5,687,429 A | 11/1997 | Rahlff | |
| 5,742,948 A | 4/1998 | Cicio | |
| 6,460,200 B1 | 10/2002 | Mottale et al. | |
| 6,547,771 B2 | 4/2003 | Robertson et al. | |
| 6,620,142 B1 | 9/2003 | Fluckiger | |
| 6,719,741 B2 * | 4/2004 | Ching | A61F 5/4556 604/329 |

(Continued)

Primary Examiner — Erin Deery
(74) Attorney, Agent, or Firm — Dunlap Bennett & Ludwig, PLLC; Brendan E. Squire

(57) ABSTRACT

A urination device includes a receptacle having a cuboid shape. The receptacle further includes a top, a bottom, a front, a back, a first side, and a second side. A top opening is defined by an inner edge at the top of the receptacle. A front opening is defined by a front edge at the front of the receptacle. An elongated v-shaped channel is defined along the bottom from the front to the back. At least a portion of the elongated v-shaped channel is disposed below the top opening.

8 Claims, 4 Drawing Sheets

(56) References Cited

U.S. PATENT DOCUMENTS

| | | | |
|---|---|---|---|
| 7,131,149 B2 * | 11/2006 | Langford | A61F 5/4556 |
| | | | 4/144.4 |
| 7,694,819 B2 | 4/2010 | Montakhabi | |
| 8,146,179 B1 | 4/2012 | Duque | |
| 9,301,870 B2 | 4/2016 | Shelton et al. | |
| 9,480,595 B2 | 11/2016 | Baham | |
| 2004/0181862 A1 | 9/2004 | Brummer et al. | |
| 2006/0218708 A1 | 10/2006 | Filsouf | |
| 2007/0044213 A1 | 3/2007 | Hall | |
| 2008/0034481 A1 | 2/2008 | Cheng | |
| 2008/0301864 A1 | 12/2008 | Brreedich-Martinez | |
| 2010/0185168 A1 | 7/2010 | Graauw et al. | |
| 2015/0000027 A1 | 1/2015 | Hughes et al. | |
| 2015/0033460 A1 | 2/2015 | Mehta | |
| 2015/0223967 A1 | 8/2015 | Rojals | |
| 2017/0273818 A1 * | 9/2017 | Pryor | A61F 5/4556 |

* cited by examiner

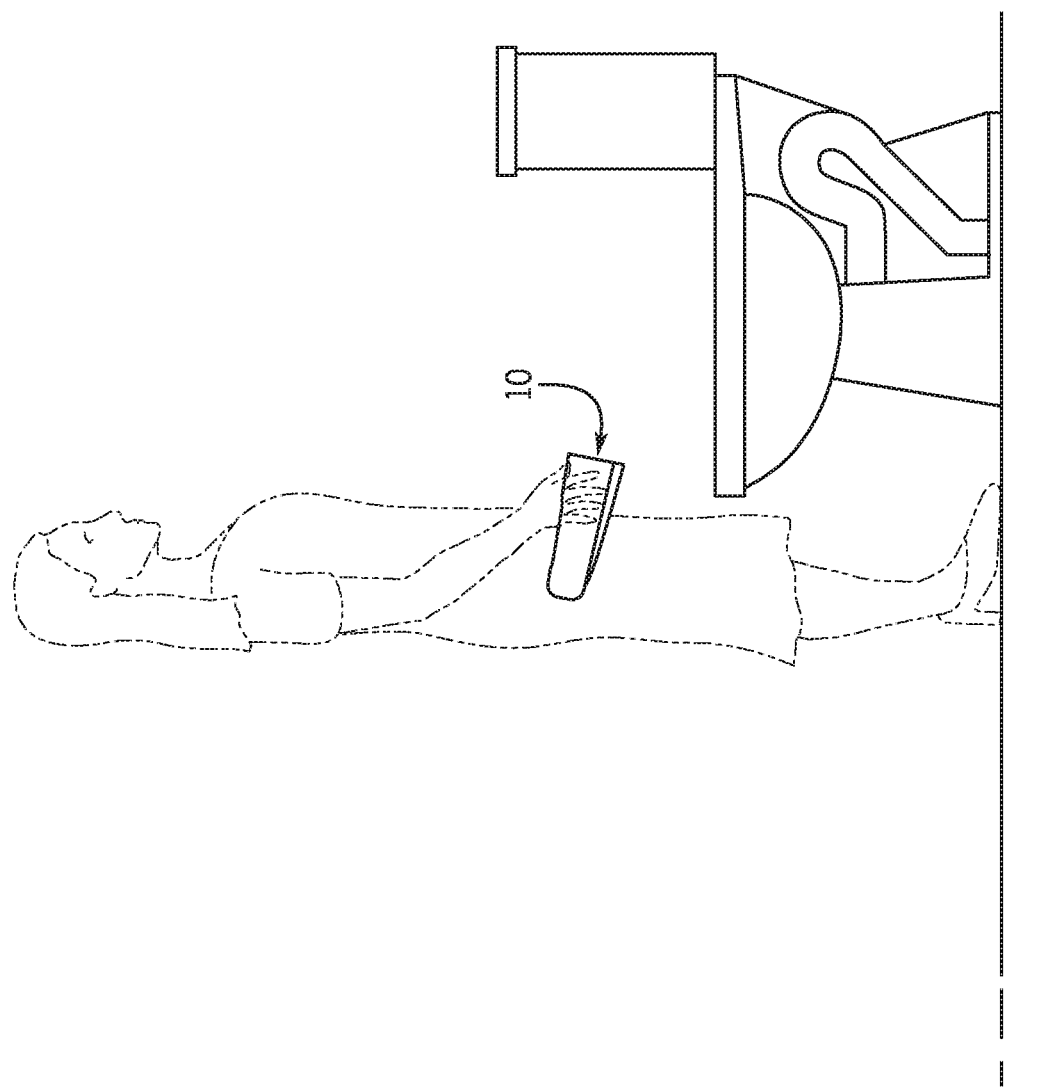

DISPOSABLE URINATION DEVICE FOR WOMEN

CROSS-REFERENCE TO RELATED APPLICATION

This application claims the benefit of priority of U.S. provisional application No. 62/545,116, filed Aug. 14, 2017, the contents of which are herein incorporated by reference.

BACKGROUND OF THE INVENTION

The present invention relates to urination devices, or more particularly, to a disposable urination device for women.

Public restroom toilets are commonly unsanitary, in which some women are apprehensive to sit on when urinating. Existing feminine urination devices are expensive and not made for low-cost mass distribution in public ladies' rooms. Many are made of long-lasting materials and are intended for multiple and/or continued use.

As can be seen, there exists a need for a more convenient, sanitary, and environmentally friendly urination device for women.

SUMMARY OF THE INVENTION

In one aspect of the present invention, a urination device comprises: a receptacle having a cuboid shape and comprising a top, a bottom, a front, a back, a first side, and a second side, wherein a top opening is defined by an inner edge at the top of the receptacle; a front opening is defined by a front edge at the front of the receptacle; and an elongated v-shaped channel is defined along the bottom from the front to the back, wherein at least a portion of the elongated v-shaped channel is disposed below the top opening.

In another aspect of the present invention, a method of urinating comprises: placing a urination device between a user's thighs, wherein the urination device comprises: a receptacle having a cuboid shape and comprising a top, a bottom, a front, a back, a first side, and a second side, wherein a top opening is defined by an inner edge at the top of the receptacle; and a front opening is defined by a front edge at the front of the receptacle; directing the front opening towards a toilet; and urinating, by the user, through the top opening of the urination device, wherein urine runs along an inner surface of the bottom of the urination device, out of the front opening, and into the toilet.

These and other features, aspects and advantages of the present invention will become better understood with reference to the following drawings, description and claims.

BRIEF DESCRIPTION OF THE DRAWINGS

FIG. 6 is a side elevation view of an embodiment of the present invention in use.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention includes a urination device that allows women to urinate from a standing position. Advantageously, this eliminates the need to sit on an unclean toilet. The rectangular shape of the present invention has rounded corners and is tapered from front to rear. The substantially rectangular shape uniquely allows the user to hold the device between her thighs. The unique shape also allows the device to be stacked or nested within other identical devices (one inside the other) and placed in a dispenser for easy access and distribution in public ladies' rooms.

Figure 1:
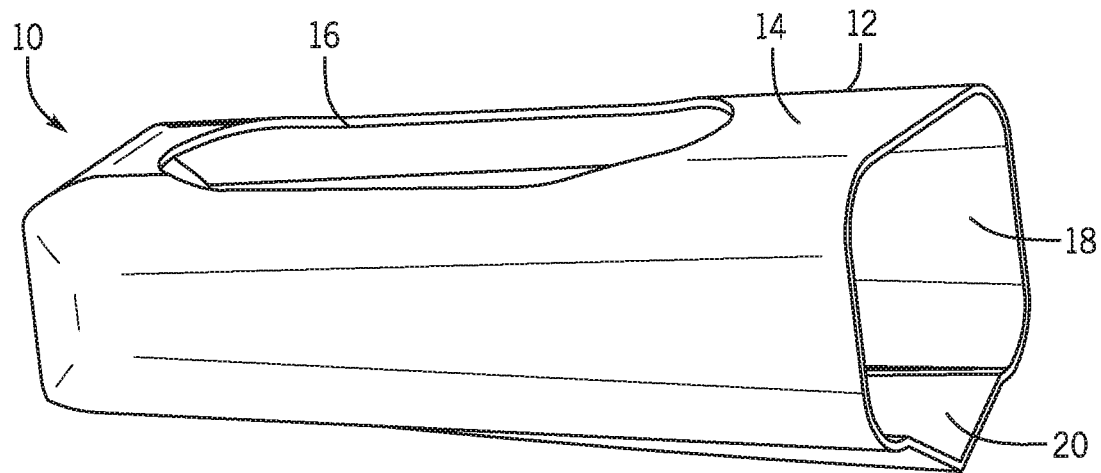
FIG. 1 is a perspective view of an embodiment of the present invention.
Figure 2:
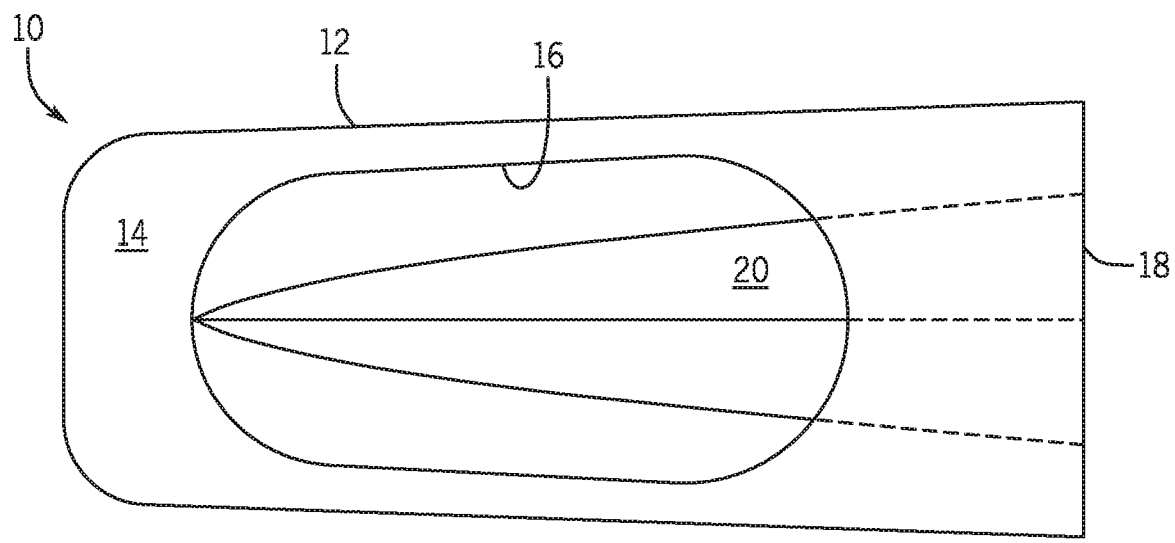
FIG. 2 is a top plan view of an embodiment of the present invention.
Figure 3:
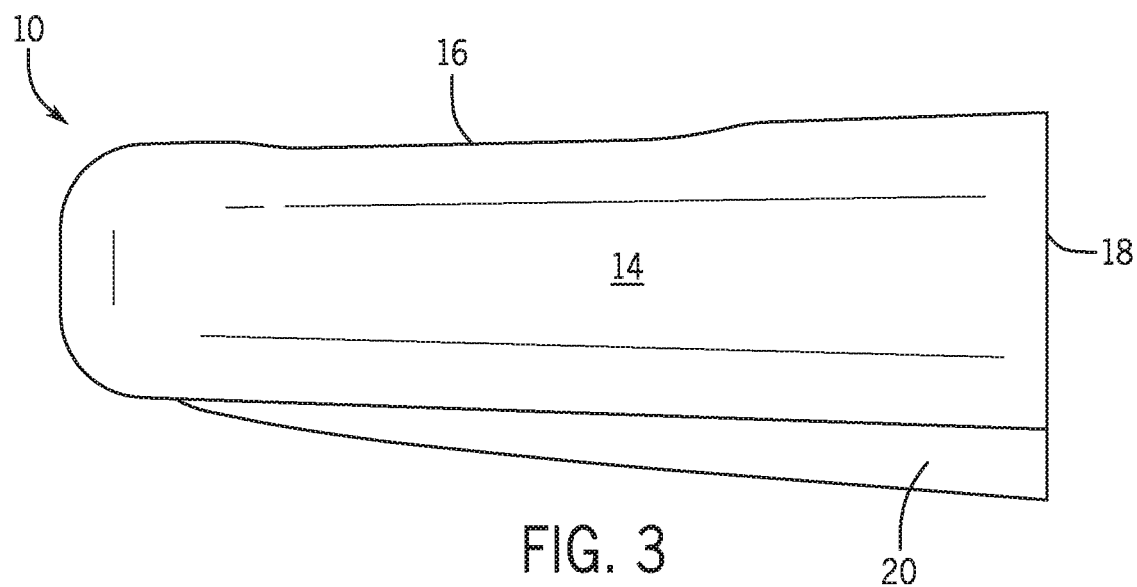
FIG. 3 is a side elevation view of an embodiment of the present invention.
Figure 4:
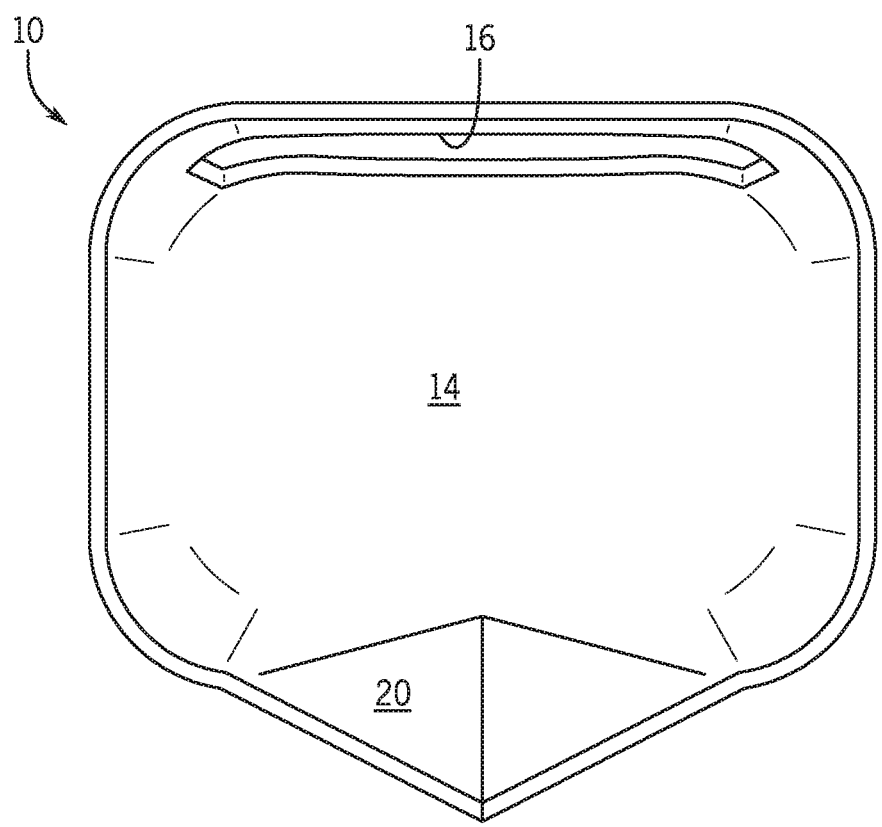
FIG. 4 is an end view of an embodiment of the present invention.
Figure 5:
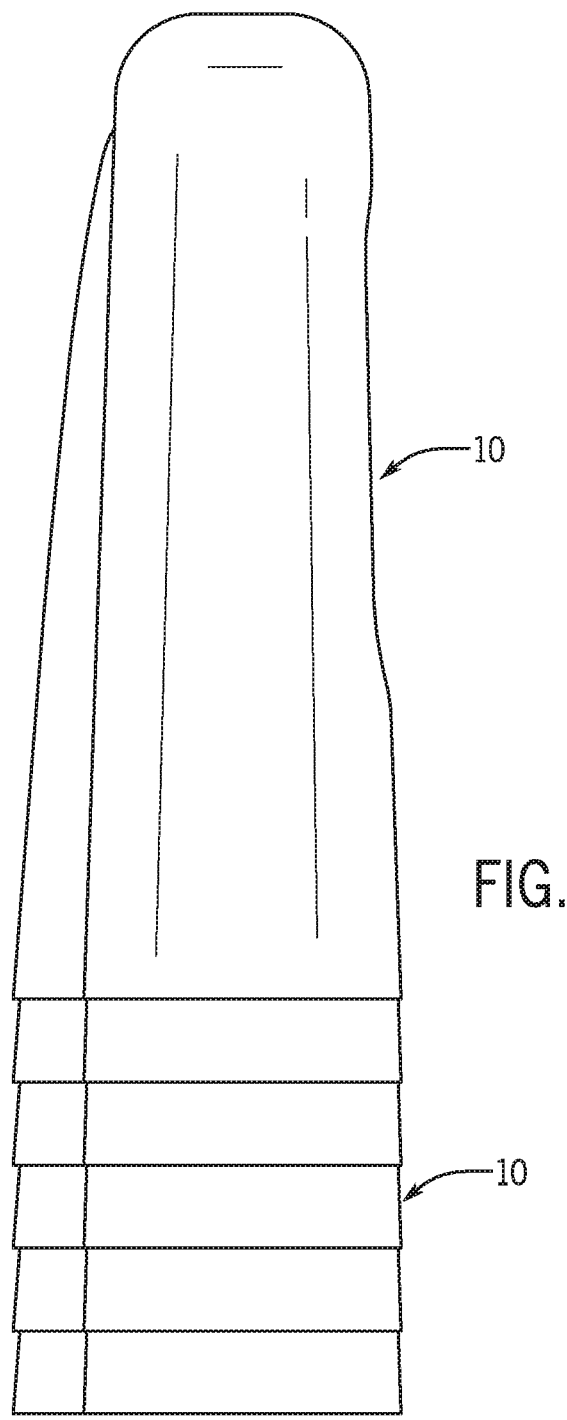
FIG. 5 is a side elevation view of an embodiment of the present invention stacked together.

Referring to FIGS. 1 through 6, the present invention includes a female urination device 10. The urination device 10 includes a receptacle 12 having a top 14, a bottom, a front, a rear, a first side, and a second side. A top opening 16 is defined by an inner edge at the top 14 of the receptacle 12. The top opening 16 is where urine from the body enters the device 10. The top 14 provides structure and strength for the device 10 and facilitates an entry-point for the urine through the top opening 16.

As mentioned above, the receptacle 12 further includes a bottom, which is opposite the top 14. The bottom receives the urine. The bottom of the device 10, which is a solid bottom wall, provides structure and strength to the device 10. The device 10 also includes a gutter 20 which is a V-shape molded into a central portion of the bottom. The gutter 20 directs the urine into a concentrated stream, thus optimizing the flow of the urine from the device 10 into the toilet.

The front of the receptacle may be open and includes a front opening 18 defined by a front edge. The rear of the receptacle 12 may be closed and includes a solid rear wall, which provides strength and structure. The rear may be substantially flat and measures approximately half the height and width of the front opening 18 of the device 10. This allows for each single device 10 to stack one inside the other. Stacks of the device 10 may be placed in a dispenser for convenient storage and dispensing to consumers. The front opening 18 of the device 10 allows urine to freely exit the device 10 into the toilet.

In certain embodiments, the first side is equal in size, shape and purpose to the second side. Both the first side and the second side are solid sidewalls that provide strength and structure to the device 10. In certain embodiments, the device 10 also includes rounded edges and corners. All edges and corners are rounded to provide comfort to the consumer during use where the device 10 may encounter the body. Additionally, the rounded edges and corners improve the ease of stacking the device for storage and dispensing.

In certain embodiments, the receptacle 12 is a tapered shape and enlarges in diameter from the rear to the front. Thus, the front opening 18 is larger than the back. For example, the front opening 18 may be approximately twice the height and width of the back. Advantageously, the tapered shape enhances the function of the V-shaped gutter 20, and allows multiple devices to be stacked one inside the other for distribution to consumers through a dispenser.

A method of using the present invention may include the following. A user holds the device 10 in place between the user's naked upper thighs approximately one inch below the outer female genitalia. The user then pulls undergarments and pants down toward the knees so that the device 10 is placed directly below the outer female genitalia. If wearing a skirt or dress, user pulls the clothing up and above the waist to prevent clothing from getting wet or interfering with the operation of the device 10. The user places her feet approximately ten to fourteen (10-14) inches apart or whatever is comfortable for the user. The user then stands close to the toilet so that the front of the device 10 extends at least three inches over the front of the toilet. The device 10 is held horizontally with the top 14 facing up and the front opening 18 facing toward the toilet. Once the device is properly positioned, no hands are needed during urination. If necessary, the user can lean slightly forward to allow optimal flow from the device into the commode. The urine flows through the top opening 16, along the V-shape of the gutter 20, out the front opening 18 and into the toilet. The user remains in this position until the bladder is empty. When urination is complete, the device 10 is removed from the body and any residual urine is emptied into the toilet. When finished, the device 10 can be disposed in an appropriate waste receptacle or recycled.

In certain embodiment, the device 10 is made with a 3-D printer, by a blow molding process, or a die-cut and press process. It is to be understood that a different process may be selected after the final material(s) have been determined. The device 10 may be made of recycled materials, biodegradable materials or materials that could be recycled after use, including but not limited to water-proof paper, waxed paper, waxed cardboard, coated cardboard, plastic that is non-porous or coated plastic, or organic materials, or coated fabric materials, or other materials that would lend themselves to this application. The entire device could be made from any one of these materials or a combination. The material can be semi-rigid or rigid. The material only needs to be thick and rigid enough so that it can withstand the normal pressure that would be applied when holding the device 10 between the thighs of the user. The outer surface of the material is ideally soft to the skin so as to be non-irritating.

Advantageously, women using the device 10 no longer need to clean the toilet seat themselves, nor do they need to stoop over the toilet while urinating, which sometimes results in soiled clothing. Stooping over a toilet while urinating usually causes dripping of urine onto the toilet seat and even onto the floor. Instead, women can remove one of these devices 10 from a dispenser located within each bathroom stall. Following the easy instructions, women can be free from the worry of exposing themselves to contamination from an unclean toilet.

In alternate embodiments, advertisements can be printed on the device to finance manufacturing costs and make it free or low cost to the consumer.

It should be understood, of course, that the foregoing relates to exemplary embodiments of the invention and that modifications may be made without departing from the spirit and scope of the invention as set forth in the following claims.

What is claimed is:

1. A urination device comprising:
   a receptacle having a polyhedron shape and comprising a top wall, a bottom wall, a back wall, a first side wall, and a second side wall, an elongated v-shaped channel defined along an inner surface of the bottom wall from a front of the receptacle to the back wall, a width of the elongated V-shaped channel increases from the back wall to the front;
   a top opening is defined by an inner edge of the top wall of the receptacle, wherein at least a portion of the elongated v-shaped channel is disposed below the top opening;
   a front opening is defined by a front edge at the front of the receptacle opposite the back wall;
   the receptacle is tapered and enlarges in diameter from the back wall to the front so that the front opening comprises a larger height and width than the back wall.

2. The urination device of claim 1, wherein the polyhedron shape is a curved polyhedron shape comprising rounded edges connecting the top wall to the first side wall, the first side wall to the bottom wall, the bottom wall to the second side wall, and the second side wall to the top wall.

3. A method of urinating comprising:
   placing a urination device between a user's thighs, wherein the urination device comprises:
      a receptacle having a polyhedron shape and comprising a top wall, a bottom wall, a back wall, a first side wall, and a second side wall, an elongated v-shaped channel defined along an inner surface of the bottom wall from a front of the receptacle to the back wall, a width of the elongated V-shaped channel increases from the back wall to the front of the receptacle, wherein
      a top opening is defined by an inner edge of the top wall of the receptacle;
      a front opening is defined by a front edge at a front of the receptacle opposite the back wall, wherein at least a portion of the elongated v-shaped channel is disposed below the top opening; and
      the receptacle is tapered and enlarges in diameter from the back wall to the front so that the front opening comprises a larger height and width than the back wall; and
   directing the front opening towards a toilet; and
   urinating, by the user, through the top opening of the urination device, wherein urine runs along an inner surface of the bottom wall of the urination device, out of the front opening, and into the toilet.

4. The method of claim 3, wherein the polyhedron shape is a curved polyhedron shape comprising rounded edges connecting the top wall to the first side wall, the first side wall to the bottom wall, the bottom wall to the second side wall, and the second side wall to the top wall.

5. A urination device comprising:
   a receptacle having a curved polyhedron shape comprising rounded edges connecting a top wall to a first sidewall, the first sidewall to a bottom wall, the bottom wall to a second side wall, and the second side wall to the top wall;
   a top opening is defined by an inner edge of the top wall of the receptacle;
   a front opening is defined by a front edge at a front of the receptacle opposite a back wall; and
   the receptacle is tapered and enlarges in diameter from the back wall to the front so that the front opening comprises a larger height and width than the back wall.

6. The urination device of claim 5, further comprising:
   an elongated v-shaped channel defined along an inner surface of the bottom wall from the front of the receptacle to the back wall, a width of the elongated V-shaped channel increases from the back wall to the front.

7. The urination device of claim 1, wherein the receptacle is configured for a nested stacking with another receptacle.

8. The urination device of claim 5, wherein the receptacle is configured for a nested stacking with another receptacle.

\* \* \* \* \*